United States Patent

Dunlap et al.

[11] Patent Number: 5,464,852
[45] Date of Patent: Nov. 7, 1995

[54] SACCHARIN DERIVATIVE PROTEOLYTIC ENZYME INHIBITORS

[75] Inventors: Richard P. Dunlap, Penfield; Albert J. Mura, Rochester; Dennis J. Hlasta, Clifton Park; Ranjit C. Desai, Colonie; Lee H. Latimer, Brighton; Chakrapani Subramanyam, East Greenbush all of N.Y.

[73] Assignee: Sterling Winthrop Inc., New York, N.Y.

[21] Appl. No.: 289,113

[22] Filed: Aug. 11, 1994

Related U.S. Application Data

[62] Division of Ser. No. 113,508, Aug. 27, 1993, Pat. No. 5,380,737, which is a continuation of Ser. No. 793,035, Nov. 15, 1991, abandoned, which is a continuation-in-part of Ser. No. 514,920, Apr. 26, 1990, abandoned, and a continuation-in-part of Ser. No. 608,068, Nov. 1, 1990, abandoned, and a continuation-in-part of Ser. No. 782,016, Oct. 24, 1991, Pat. No. 5,128,339, said Ser. No. 514,920, Apr. 26, 1990, abandoned, is a continuation-in-part of Ser. No. 347,125, May 4, 1989, abandoned, and a continuation-in-part of Ser. No. 347,126, May 4, 1989, abandoned, said Ser. No. 782,016, Oct. 24, 1991, Pat. No. 5,128,339, is a continuation-in-part of Ser. No. 608,068, Nov. 1, 1990, abandoned.

[51] Int. Cl.[6] .................... A71K 31/425; A71K 31/41; C07D 249/04; C07D 275/06
[52] U.S. Cl. .................... 514/373; 548/210; 546/200; 544/135; 544/368; 514/239.5; 514/254; 514/321
[58] Field of Search ................ 548/210; 514/373

[56] References Cited

U.S. PATENT DOCUMENTS

| | | | |
|---|---|---|---|
| 4,195,023 | 3/1980 | Mulvey et al. | 548/209 |
| 4,263,393 | 4/1981 | Chen | 430/218 |
| 4,276,298 | 6/1981 | Jones et al. | 424/270 |
| 4,350,752 | 9/1982 | Reczek et al. | 430/219 |

FOREIGN PATENT DOCUMENTS

WO9013549  11/1990  WIPO .

OTHER PUBLICATIONS

Choi et al., J. Heterocyclic Chem. 1989, 26, 1073–1076.

Primary Examiner—Johann Richter
Assistant Examiner—Laura Cross
Attorney, Agent, or Firm—Michael D. Alexander; Paul E. Dupont

[57] ABSTRACT

Compounds having the structural formula

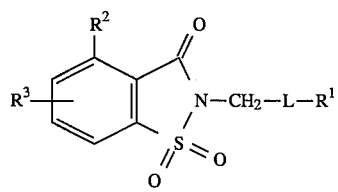

Formula I wherein

L is N, O or $SO_n$ wherein n is 0, 1 or 2;

L—$R^1$ is a leaving group, H—L—$R^1$ is the conjugate acid thereof and, when L is N, H—L—$R^1$ has a $pK_a$ value less than or equal to 6, when L is O, H—L—$R^1$ has a $pK_a$ value less than or equal to to 8, and when L is $SO_n$, H—L—$R^1$ has a $pK_a$ value less than or equal to 5;

$R^2$ is primary or secondary alkyl of two to four carbon atoms, primary alkylamino of one to three carbon atoms, primary alkylmethylamino of two to four carbon atoms, diethylamino or primary alkoxy of one to three carbon atoms; and $R^3$ is from one to three of a variety of substituents at any or all of the 5-, 6- and 7-positions;

or a pharmaceutically acceptable acid addition salt thereof if the compound has a basic functional group or a pharmaceutically acceptable base addition salt thereof if the compound has an acidic functional group, which inhibit the enzymatic activity of proteolytic enzymes, and processes for preparation thereof, method of use thereof in treatment of degenerative diseases and pharmaceutical compositions thereof are disclosed.

18 Claims, No Drawings

SACCHARIN DERIVATIVE PROTEOLYTIC ENZYME INHIBITORS

This application is a division of our prior application Ser. No. 08/113,508, filed on Aug. 27, 1993, now U.S. Pat. No. 5,380,737, issued Jan. 10, 1995; which in turn is a continuation of our prior application Ser. No. 07/793,035, filed Nov. 15, 1991, now abandoned; which in turn is a continuation-in-part of our three following prior applications: application Ser. No. 07/514,920, filed Apr. 26, 1990, now abandoned, application Ser. No. 07/608,068, filed Nov. 1, 1990, now abandoned, and application Ser. No. 07/782,016, filed Oct. 24, 1991, now U.S. Pat. No. 5,128,239, issued Jul. 7, 1992. Application Ser. No. 07/514,920 is a continuation-in-part of application Ser. No. 07/347,125 and application Ser. No. 07/347,126, which were both filed May 4, 1989 and are both now abandoned. Application Ser. No. 07/782,016 is a continuation-in-part of application Ser. No. 07/608,068 which is now abandoned.

BACKGROUND OF THE INVENTION

1. Field of the Invention

The invention relates to saccharin derivatives which inhibit the enzymatic activity of proteolytic enzymes, to processes for preparation thereof, to method of use thereof in treatment of degenerative diseases and to pharmaceutical compositions thereof.

2. Information Disclosure Statement

Inhibitors of proteolytic enzymes are useful in treatment in degenerative disorders such as emphysema, rheumatoid arthritis and pancreatitis in which proteolysis is a substantive element. Serine proteases are the most widely distributed class of proteolytic enzymes. Some serine proteases are characterized as chymotrypsin-like or elastase-like based upon their substrate specificity. Chymotrypsin and chymotrypsin-like enzymes normally cleave a peptide bond in a protein at a site at which the amino acid on the carbonyl side is Trp, Tyr, Phe, Met, Leu or other amino acid which contains an aromatic or a large alkyl side chain. Elastase and elastase-like enzymes normally cleave a peptide bond at a site at which the amino acid residue on the carbonyl side of the bond is Ala, Val, Ser, Leu or other small amino acid. Both chrmotrypsin-like and elastase-like enzymes are found in leukocytes, mast cells and pancreatic juice in higher organisms, and are secreted by many types of bacteria, yeast and parasites.

Mulvey et al. U.S. Pat. No. 4,195,023 issued Mar. 25, 1980 describes methods of inhibiting elastase and treating emphysema with 4, 5, 6 or 7-$R_1$-2-$R_2$CO- 1,2-benzisothiazolinone- 1,1-dioxide (4, 5, 6 or 7-$R_1$-2-$R_2$CO-saccharin) wherein $R_1$ is halogen, alkoxy, alkylamino, dialkylamino, alkoxycarbonyl, amino, nitro or especially hydrogen and $R_2$ is hydrogen, alkyl, alkenyl, alkynyl, cycloalkyl, halophenyl, heteroaryl or substituted heteroaryl, for example 2-(2-furoyl)saccharin, and pharmaceutical compositions thereof.

Chen U.S. Pat. No. 4,263,393 issued Apr. 21, 1981 describes 2-aroylmethylsaccharins substituted or unsubstituted on aroyl and on the saccharin nucleus including for example as compound 12 2-[(p-fluorobenzoyl)methyl]saccharin as being "useful in photographic elements, film units and processes to provide electrons to immobile compounds which must accept at least one electron before releasing a diffusible dye or photographic reagent."

Jones et al U.S. Pat. No. 4,276,298 issued Jun. 30, 1981 describes 2-R-1,2-benzisothiazolinone- 1,1-dioxides (2-R-saccharin) wherein R is phenyl or pyridyl substituted by from one to five of fluoro, nitro except mononitro when R is phenyl, trifluoromethyl, cyano, alkoxycarbonyl, alkylcarbonyl, carboxyl, carbamoyl, alkylacylamino, alkylsulfonyl, N,N-dialkylsulfamyl, trifluoromethoxy, trifluoromethylthio, trifluoromethylsulfonyl and trifluoromethylsulfinyl "useful in methods of inhibiting proteases, especially elastase, and of treating emphysema rheumatoid arthritis, and other inflammatory diseases."

Reczek et al. U.S. Pat. No. 4,350,752 issued Sep. 21, 1982 describes 2-(heterocyclymethyl)saccharins substituted for unsubstituted on heterocyclyl and on the saccharin nucleus including for example as compound 28 2-[(1-phenyltetrazol-5-yl)thiomethyl]saccharin as "blocked photographic reagents . . . useful in photographic elements, film units and processes."

Dunlap et al. PCT Application WO 90/13549 published Nov. 15, 1990 describes saccharin derivatives useful as proteolytic enzyme inhibitors having the structural formula:

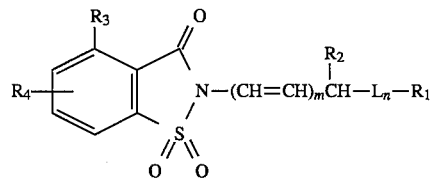

wherein:

L is —O—, —S—, —SO— or —$SO_2$—;

m and n are each independently 0 or 1;

$R_1$ is halogen, lower-alkanoyl, 1-oxo-phenalkenyl, phenyl (or phenyl substituted by halogen, lower-alkyl, lower-alkoxy, nitro, amino, lower-alkylamino or di-lower-alkyl-amino) or heterocyclyl selected from 1H-(5-tetrazolyl), 5-oxo-1-tetrazolyl, 5-thioxo-1-tetrazolyl (when $R_2$ as defined hereinbelow is other than phenylthio), pyrimidinyl, 2-benzoxazolyl, 2-enzothiazolyl, 2-phthalimidyl, 2-(1,3,4-thiadiazolyl), 5-(1,2,4-thiadiazolyl), 5-thioxo-3-(1,2,4-thiadiazolyl), 4-(5-oxo-1,3,4-thiadiazolyl), 4-5-thioxo- 1,3,4-thiadiazolyl), 3-(1,2,4-thiazolyl), 4-(1,2,4-triazolyl), (1,2,3-triazolyl), 2-imidazolyl or 3-(1,2,4-triazolo[4,3-a]pyridinyl), or such heterocyclyl groups substituted on any available nitrogen atom by lower-alkyl, hydroxy-lower-alkyl, cycloalkyl, 2-, 3- or 4-pyridinyl, carboxy-lower-alkyl, lower-alkoxycarbonyl-lower-alkyl, aminocarbonyl-lower-alkyl, lower-alkylaminmocarbonyl-lower-alkyl, di-lower-alkylamino-carbonyl-lower-alkyl, amino-lower-alkyl, lower-alkylamino-lower-alkyl, di-lower alkylamino-lower-alkyl, 4-morpholinyl-lower-alkyl, 1-piperidinyl-lower-alkyl, 1-pyrrolidinyl-lower-alkyl or phenyl (or phenyl substituted by amino, lower-alkyl-amino, di-lower-alkylamino, lower-alkanamido, N-lower-alkyl-lower-alkanamido, carboxy-lower-alkanamido, carboxy, carbo-lower-alkoxy, lower-alkoxy or halogen), or such heterocyclyl groups substituted on any available carbon atom by nitro, lower-alkyl, amino, lower-alkylamino, di-lower-alkylamino, cycloalkylamino, mercapto, lower-alkylthio, amino-lower-alkylthio, lower-alkylamino-lower-alkylthio, di-lower-alkyl-amino-lower-alkylthio, 4-morpholinyl-lower-alkylthio, 1-piperidinyl-lower-alkylthio, 1-pyrrolidinyl-lower-alkylthio, carbo-lower-alkoxy or phenyl (or phenyl substituted by amino, lower-alkylamino, di-lower-alkylamino, lower-alkanamido, N-lower-alkyl-lower-alkanamido, lower-alkyl, lower-alkoxy or halogen);

$R_2$ is hydrogen, carbo-lower-alkoxy, phenyl or phenylthio;

$R_3$ is hydrogen, halogen, primary or secondary lower-alkyl, lower-alkoxy, carbo-lower-alkoxy, phenyl, fluoro-lower-alkyl, lower-alkenyl or cyano;

$R_4$ is hydrogen or from one to two substituents selected from halogen, cyano, nitro, amino, lower-alkanamido, phenyl-lower-alkanamido, diphenyl-lower-alkanamido, lower-alkylsulfonylamino, polyfluoro-lower-alkylsulfonylamino, aminosulfonyl, lower-alkyl, polyhalo-lower-alkyl, cycloalkyl, polyhalo-lower-alkoxy, hydroxy, lower-alkoxy, carboxy, hydroxymethyl, formyl, aminomethyl, lower-alkylsulfonyl, polyhalo-lower-alkylsulfonyl, lower-alkylsulfonyl-aminosulfonyl and lower-alkoxypoly-lower-alkyleneoxy; and wherein the —$CHR_2$— group is always appended either to a hetero atom of the L moiety as defined above or it is appended to a hetero atom of the $R_1$ moiety, with the provisos that (i) when m and n are 0 and $R_2$, $R_3$ and $R_4$ are all hydrogen, $R_1$ cannot be halogen; (ii) when m is 0, n is 1, L is -S- and $R_2$, $R_3$ and $R_4$ are each hydrogen, $R_1$ cannot be 1-phenyl-1H-(5-tetrazolyl); (iii) when m is 0, n is 1, L is —O— or —S— and $R_2$, $R_3$ and $R_4$ are all hydrogen, $R_1$ cannot be lower-alkanoyl; (iv) when m is 0, n is 1, L is —O—, —S— or —SO—, and $R_2$, $R_3$ and $R_4$ are all hydrogen, or when m is O, n is 1, L is —S—, $R_2$ and $R_4$ are hydrogen and $R_3$ is halogen, or when m is O, n is 1, L is —SO— or —$SO_2$—, $R_2$ is carbo-lower-alkoxy and $R_3$ and $R_4$ are both hydrogen, $R_1$ cannot be phenyl or substituted phenyl.

SUMMARY OF THE INVENTION

In a first composition of matter aspect the invention is a compound having the structural formula

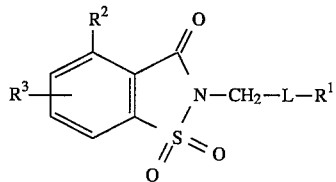

Formula I wherein

L is N, O or $SO_n$ wherein n is 0, 1 or 2;

L—$R^1$ is a leaving group, H—L—$R^1$ is the conjugate acid thereof and, when L is N, H—L—$R^1$ has a $pK_a$ value less than or equal to 6, when L is O, H—L—$R^1$ has a $pK_a$ value less than or equal to to 8, and when L is $SO_n$, H—L—$R^1$ has a $pK_a$ value less than or equal to 5;

$R^2$ is primary or secondary alkyl of two to four carbon atoms, primary alkylamino of one to three carbon atoms, primary alkylmethylamino of two to four carbon atoms, diethylamino or primary alkoxy of one to three carbon atoms; and $R^3$ is from one to three substituents at any or all of the 5-, 6- and 7-positions and is selected from the group consisting of hydrogen, lower-alkyl, cycloalkyl, amino-lower-alkyl, lower-alkylamino-lower-alkyl, di-lower-alkylamino-lower-alkyl, hydroxy-lower-alkyl, lower-alkoxy-lower-alkyl, perfluoro-lower-alkyl, perchloro-lower-alkyl, formyl, cyano, carboxy, aminocarbonyl, R-oxycarbonyl, B=N wherein B=N is amino, lower alkylamino, di-lower-alkylamino, carboxy-lower-alkylamino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl, 1-lower-alkyl-2-pyrrolyl, lower-alkylsulfonylamino, perfluoro-lower-alkylsulfonylamino, perchloro-lower-alkylsulfonylamino, nitro, hydroxy, lower-alkoxy, cycloalkoxy, B=N-lower-alkoxy, hydroxy-lower-alkoxy, poly-lower-alkoxy-lower-alkoxy, hydroxy-poly-alkylenoxy, lower-alkoxy-poly-lower-alkylenoxy, B=N-carbonyloxy, carboxy-lower-alkoxy, R-oxycarbonyl-lower-alkoxy, methylenedioxy, di-lower-alkylphosphonyloxy, R-thio, R-sulfinyl, R-sulfonyl, perfluoro-lower-alkylsulfonyl, perchloro-lower-alkylsulfonyl, aminosulfonyl, lower-alkylaminosulfonyl, di-lower-alkylaminosulfonyl and halo wherein R is lower-alkyl, phenyl, benzyl or naphthyl or phenyl or naphthyl having one or two substituents selected from the group consisting of lower-alkyl, lower-alkoxy and halo;

or a pharmaceutically acceptable acid addition salt thereof if the compound has a basic functional group or a pharmaceutically acceptable base addition salt thereof if the compound has an acidic functional group.

The compounds of Formula I inhibit the enzymatic activity of proteolytic enzymes and are useful in treatment of degenerative diseases.

In a first process aspect the invention is the process for preparing a compound of Formula I which comprises condensing the corresponding compound having the structural formula

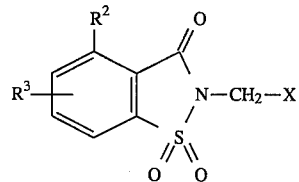

Formula II wherein X is chloro or bromo with the corresponding compound of formula H—L'—$R^1$ in the presence of a base or with a corresponding basic salt of the compound of formula H—L'—$R^1$ wherein L' is N, O or S to prepare the corresponding compound of Formula I wherein L is N, O or S and then oxidizing with one molar equivalent of a peroxide or peracid the corresponding compound of Formula I wherein L is S to prepare the compound of Formula I wherein L is SO or with one or two molar equivalents of a peroxide of peracid the corresponding compound of Formula I wherein L is SO or S respectively to prepare the compound of Formula I wherein L is $SO_2$.

In a second process aspect the invention is the process for preparing a compound of Formula I which comprises condensing the corresponding compound of formula X—$CH_2$—L'—$R^1$ wherein X is chloro or bromo and L' is N, O or S with the corresponding compound having the structural formula

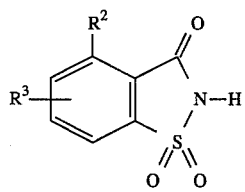

Formula III in the presence of a base or with a basic salt thereof to prepare the corresponding compound of Formula I wherein L is N, O or S and then oxidizing with one molar equivalent of a peroxide or peracid the corresponding compound of Formula I wherein L is S to prepare the compound of Formula I wherein L is SO or with one or two molar equivalents of a peroxide or peracid the corresponding compound of Formula I wherein L is SO or S respectively to prepare the compound of Formula I wherein L is $SO_2$.

In a third process aspect of the invention is the process for preparing a compound of Formula I wherein L is O and $R^1$ is acyl which comprises condensing the corresponding compound having the structural formula

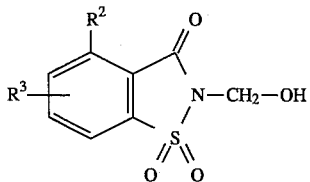

Formula IV with the corresponding acid chloride of formula Cl—$R^1$ or the corresponding acid anhydride of formula $O(R^1)_2$ in the presence of a strong acid catalyst.

In a fourth process aspect the invention is the process for preparing a compound of Formula I wherein L—$R^1$ is substituted or unsubstituted 1,2,3-triazol-1-yl which comprises condensing the corresponding compound of Formula II with an alkali metal azide and then effecting cycloaddition of the resulting 2-azidomethyl-4-$R^2$-5,6 or 7-$R^3$-saccharin with the corresponding substituted or unsubstituted acetylene.

In a fifth process aspect the invention is the method of treating a patient having a degenerative disease which comprises administering to the patient a proteolytic enzyme inhibiting amount of a compound of Formula I.

In a second composition of matter aspect the invention is a pharmaceutical composition for treatment of degenerative disease which comprises a proteolytic enzyme inhibiting concentration of a compound of Formula I in a pharmaceutical carrier.

DETAILED DESCRIPTION OF THE INVENTION INCLUSIVE OF THE PREFERRED EMBODIMENTS

The Compounds and Their Preparation

Saccharin is 1,2-benzisothiazol-(1H)-3-one-1,1-dioxide and the compounds of Formula I, which are 2-($R^1$—L—$CH_2$)-4-$R^2$-(5,6 and/or 7)-$R^3$- 1,2-benzisothiazol-(1H)-3-one-1,1-dioxides, are accordingly 2-($R^1$—L—$CH_2$)-4-$R^2$-(5,6 and/or 7)-$R^3$-saccharins.

In the compounds of Formulas I–IV "corresponding" means that a defined variable in one formula has the same definition in another formula.

When L is N, N taken together with $R^1$ is N-heterocyclyl, that is, N is part of a heterocyclic ring and is the atom whereby the heterocyclic ring is bonded to $CH_2$. N-Heterocyclyl is preferably monocyclic or bicyclic, substituted or unsubstituted, aromatic or hydroaromatic N-heterocyclyl, most preferably monocyclic, substituted, aromatic N-heterocyclyl, for example 4,5-di(t-butylsulfonyl)-1,2,3-triazol-1-yl. When L is O, the bond between L and $R^1$ is an ester or ester-like bond or an ether or ether-like bond. If it is an ester or ester-like bond, $R^1$ is preferably acyl wherein acyl is lower-alkanoyl or an amino acid or peptide acyl or cycloalkanecarbonyl or monocyclic, bicyclic or tricyclic aryl-lower-alkanoyl unsubstituted or substituted in alkanoyl by hydroxy or monocyclic or bicyclic, substituted or unsubstituted, aromatic or hydroaromatic C-heterocyclcarbonyl, monocyclic substituted or unsubstituted aryloxy-2-lower-alkanoyl or more preferably monocyclic, bicyclic or tricyclic, substituted or unsubstituted aroyl, most preferably monocyclic substituted or unsubstituted aroyl, or B'=N-carbonyl wherein B'=N is amino, lower-alkylamino, di-lower-alkylamino, aryl-lower-alkylamino, diarylamino, 1-pyrrolidinyl, 1-piperidinyl, 1-morpholinyl, 1-pieperazinyl, 4-lower-alkyl-1-piperazinyl or 1-azepinyl. If it is an ester or ester-like bond, $R^1$ is also preferably (mono or di-lower-alkyl, phenyl or lower-alkoxyphenyl)phosphinyl or (mono or di-lower-alkyl, phenyl or phenyl-lower-alkyl)phosphono. If it is an ether or ether-like bond, $R^1$ is preferably monocyclic or bicyclic, substituted or unsubstituted, aromatic or hydroaromatic C-heterocyclyl or the residue of an oxime or more preferably monocyclic, bicyclic or tricyclic, substituted aryl or monocyclic or bicyclic, substituted or unsubstituted, aromatic or hydroaromatic 3-oxycarbonyl-1-enyl or 3-oxo-C-heterocycl-1-enyl. When L is S, the bond between L and $R^1$ is a thioester or thioether or thiocarbonate bond and H—L—$R_1$ is a thioacid or thios or thiocarbonate and $R^1$ is preferably cyano or lower-alkoxythiocarbonyl or monocyclic, bicyclic or tricyclic, substituted or unsubstituted aroyl or aryl or preferably monocyclic or bicyclic, substituted or unsubstituted, aromatic or hydroaromatic C-heterocyclyl, most preferably monocyclic, substituted, aromatic C-heterocyclylcarbonyl the heterocyclic ring is bonded to $CH_2$ and carbonyl respectively at a carbon atom of the heterocyclic ring.

In lower-alkyl, perfluoro-lower-alkyl, perchloro-lower-alkyl, lower-alkoxycarbonyl, lower-alkylamino, di-lower-alkylamino, lower-alkoxy, the lower-alkylamino part of lower alkylamino-lower-alkyl, the lower-alkylamino part of di-lower-alkylamino-lower-alkyl, the lower-alkoxy part of lower-alkoxy-lower alkyl, carboxy-lower-alkylamino, 4-lower-alkyl-1-piperazinyl, 1-lower-alkyl-2-pyrrolyl, lower-alkylsulfonylamino, perfluoro-lower-alkylsulfonylamino, perchloro-lower-alkylsulfonylamino, the first lower-alkoxy part of lower-alkoxy-lower-alkoxy, the first lower-alkoxy part of poly-lower-alkoxy-lower-alkoxy, the lower-alkoxy part of lower-alkoxy-poly-lower-alkylenoxy, R-oxycarbonyl-lower-alkoxy, perfluoro-lower-alkylsulfonyl, perchloro-lower-alkylsulfonyl, lower-alkylaminosulfonyl and di-lower-alkylaminosulfonyl the carbon chain part thereof has from one to ten carbon atoms, preferably from one to four carbon atoms, and is branched or unbranched. In amino-lower-alkyl, the lower-alkyl part of lower-alkylamino-lower-alkyl, the lower-alkyl part of di-lower-alkylamino-lower-alkyl, hydroxy-lower-alkyl, the lower-alkyl part of lower-alkoxy-lower-alkyl, the lower-alkoxy part of N=B-lower-alkoxy, hydroxy-lower-alkoxy, polyhydroxy-lower-alkoxy, the second lower-alkoxy part of loweralkoxy-lower-alkoxy, the second lower-alkoxy part of poly-lower-alkoxy-lower-alkoxy, the alkylenoxy part of hydroxy-poly-lower-alkylenoxy, the alkylenoxy part of lower-alkoxy-poly-lower-alkylenoxy and lower-alkanoyl the carbon chain part thereof has from two to ten carbon atoms, preferably from two to four carbon atoms, and is branched or unbranched. Alkylene is preferably 1,2-alkylene. Cycloalkyl, cycloalkoxy and cycloalkanoyl have from three to six ring carbon atoms and can be substituted by one or more lower-alkyl. Halo is fluoro, chloro, bromo or iodo. Monocyclic aryl is phenyl. Bicyclic aryl is naphthyl. Tricyclic aryl is anthracyl or phenanthryl. Aryl and aroyl can be substituted by lower-alkyl, lower-alkoxy or halo. 3-Oxycarbonyl-1-enyl and 3-oxo-C-heterocycl- 1-enyl have from four to ten ring carbon atoms and can be substituted by one or more lower-alkyl or other substituent.

$R^2$ is preferably primary or secondary alkyl of two to four carbon atoms.

$R^3$ is preferably hydroxy, lower-alkoxy, cycloalkoxy, B=N-lower-alkoxy, hydroxy-lower-alkoxy, polyhydroxy-lower-alkoxy or acetal or ketal thereof, lower-alkoxy-lower-alkoxy, poly-lower-alkoxy-lower-alkoxy, lower-alkoxy-poly-lower-alkoxy, B=N-carbonyloxy, carboxy-lower-alkoxy, R-oxycarbonyl-lower-alkoxy, methylenedioxy or di-lower-alkylphosphonyloxy and, except methylenedioxy, is preferably located at the 6-position. Methylenedioxy can be located at the 5 and 6- or 6 and 7-positions.

In carrying out preparation of a compound of Formula I from a corresponding compound of Formula II and the corresponding H—L'—$R^1$ or a corresponding compound of Formula III and the corresponding X—CH$_2$—L'—$R^1$ in the presence of a base the base can be any base which is not itself a reactant under the reaction conditions and is preferably an alkali metal carbonate, an alkali metal alkoxide, a tri-lower-alkylamine, a thallous lower-alkoxide, 1,8-diazabicyclo[5.4.0]undec-7-ene or 7-emthyl-1,5,7-triabicyclo[4.4.0]dec-5-ene. Under the reaction conditions the base may form the basic salt of H—L'—$R^1$ or the compound of Formula III, which then reacts with the compound of Formula II or X—CH$_2$—L'—$R^1$ respectively. The basic salt of H—L'—$R^1$ or the compound of Formula III can also be formed separately and then condensed with the compound of Formula II or X—CH$_2$—L'—$R^1$ respectively and is preferably an alkali metal, especially cesium, or thallous salt thereof. The condensation is carried out in an organic solvent or mixture of organic solvents inert under the reaction conditions, for example acetone, methyl ethyl ketone, acetonitrile, tetrahydrofuran, diethyl ether, dimethylformamide, N-methyl[pyrrolidone, dichloromethan, xylene, toluene or a lower-alkanol or mixture thereof, at a temperature in the range from ambient temperature to the boiling temperature of the solvent or solvent mixture.

In carrying out preparation of a compound of Formula I from a corresponding compound of Formula IV and the corresponding acid chloride Cl—$R^1$ or the corresponding acid anhydride O($R^1$)$_2$ the strong acid catalyst is any strong acid catalyst which does not otherwise react with the compound of Formula I or the compound of Formula IV, for example sulfuric acid or p-toluenesulfonic acid. The condensation is carried with or without an organic solvent inert under the reaction conditions or a mixture thereof at a temperature of 0°–100° C.

A compound of Formula I wherein L is SO or SO$_2$ can be prepared using any peroxide or peracid which does not oxidize any other part of the molecule in an inert solvent with or without heating or cooling. The preferred peroxide or peracid is m-chloroperbenzoic acid.

In preparing a compound of Formula I wherein L—$R^1$ is substituted or unsubstituted 1,2,3-triazol-1-yl the alkali metal azide is preferably sodium azide. Condensation of the corresponding compound of Formula II with the alkali metal azide is carried out with or without heating or cooling, preferably at room temperature, in an inert solvent, for example benzene, toluene or dimethylformamide, optionally using a crown ether, for example 18-crow-6 ether. Cyclization of the resulting 2-azidomethyl-4-$R^2$-5,6 or 7-$R^3$-saccharin with the corresponding substituted or unsubstituted acetylene is preferably carried out in the same inert solvent with heating.

The compounds of Formulas II, II and IV and of formulas H—L—$R^1$, X— CH$_2$—L—$R^1$, Cl—$R^1$ and O($R^1$)$_2$ are known or are made by known methods or by methods described below.

A compound of Formula III can be prepared by diazotizing the corresponding lower-alkyl 2-amino-3,4 or 5-$R^3$-6-$R^4$-benzoate ester, chlorosulfonylating the resulting lower-alkyl 3, 4 or 5-$R^3$-6-$R^4$-benzoate ester 2-diazonium salt with sulfur dioxide and cuprous chloride, and cyclizing the resulting lower-alkyl 2-chlorosulfonyl-3,4 or 5-$R^3$-6-$R^4$ benzoate ester with ammonia. Hydroxy-methylation of the resulting compound of Formula III with formaldehyde affords the corresponding compound of Formula IV, displacement of whose hydroxyl with chloride or bromide using, for example tionyl chloride, thionyl bromide, phosphorus trichloride or phosphorus tribromide affords the corresponding compound of Formula II.

A compound of Formula II can also be prepared by phenylthiomethylating the corresponding compound of Formula III or basic salt thereof with phenyl chloromethyl sulfide and displacing phenylthio from the resulting 2-phenylthiomethyl-4-$R^2$-5,6 or 7-$R^3$-saccharin with chloride or bromide using, for example, sulfuryl chloride or sulfuryl bromide.

A compound of Formula II wherein X is chloro can also be prepared in one step from the corresponding compound of Formula III by chloromethylation with formaldehyde and chlorotrimethylsilane in the presence of stannic chloride.

A compound of Formula III can also be prepared by lithiating the corresponding 2-$R^2$-3,4 or 5-$R^3$-N,N-di-lower alkylbenzamide with a lower-alkyl lithium, aminosulfonylating the resulting 2-$R^2$-3,4 or 5-$R^3$-6-lithio-N,N-di-lower-alkylbenzamide with sulfur dioxide followed by hydroxylamine O-sulfonic acid or sulfuryl chloride followed by ammonia, and cyclizing the resulting 2-$R^2$-3, 4 or 5-$R^3$-6-aminosulfonyl-N,N-di-lower-alkylbenzamide in refluxing acetic acid.

A compound of Formula III wherein $R^2$ is primary or secondary alkyl of two to four carbon atoms can be prepared by lithiating the corresponding 4-methyl-5, 6 or 7-$R^3$-saccharin with two molar equivalents of a lower-alkylthium in an inert solvent, for example tetrahydrofuran, and alkylating the resulting 4-lithiomethyl-5, 6 or 7-$R^3$-saccharin with the appropriate alkyl halide. Both reactions are carried out at a temperature in the range from –80° C. to –50° C. The above-described 2-$R^2$-3, 4 or 5-$R^3$-N,N-di-lower-alkylbenzamide wherein $R^2$ is primary or secondary alkyl of two to four carbon atoms can be prepared by a similar lithiation-alkylation sequence starting with the corresponding 2-methyl, ethyl or propyl-3,4 or 5-$R^3$-N,N-di-lower-alkylbenzamide.

A compound of Formula III wherein $R^2$ is primary or secondary alkyl of two to four carbon atoms can also be prepared by introducing $R^2$ earlier in the synthesis. Conjugate addition of the appropriate $R^2$-cuprate to 2-cyclohexenone and methoxycarbonylation of the resulting copper enolate with methyl cyanoformate gives the corresponding 2-methoxycarbonyl-3-$R^2$-cyclohexanone, enol etherification of which with benzylthiol and acidic clay gives a mixture of the corresponding 6-$R^2$-2-benzylthiol-1-cyclohexenecarboxylic acid methyl ester and 6-$R^2$-2-benzylthio-3-cyclohexenecarboxylic acid methyl ester, aromatization of which with dichlorodicyanobenzoquinone gives the corresponding 2-$R^2$-6-benzylthiobenzoic acid methyl ester, oxidation-chlorination-debenzylation of which with chlorine in aqueous acetic acid gives 2-$R^2$-6-chlorosulfonylbenzoic acid methyl ester, cyclization of which with ammonia gives the corresponding 4-$R^2$-saccharin of Formula III.

Preparation of certain compounds of Formula III requires building up both rings thereof. For example, to prepare a compound of Formula III wherein $R^2$ is lower-alkoxy and $R^3$ is hydroxy, 3,3-thiobispropionic acid is converted with thionyl chloride into the bis acid chloride, which is converted with benzylamine into the bis benzylamide, which on cyclization with sulfuryl chloride gives 5-chloro-2-benzyl-2H-isothiazol-3-one, which on oxidation with one molar equivalent of a peracid gives 5-chloro-2-benzyl-2H-isothiazol- 3-one-1-oxide, which on heating under pressure with a 2-lower-alkoxyfuran gives a 4-lower-alkoxy-7-hydroxy-2-benzyl-1,2-benzoisothiazol-2H-3-one-1-oxide, which on oxidation with one molar equivalent of a peracid gives the corresponding 4-lower-alkoxy- 7-hydroxy-2-benzyl-1,2-benzoisothiazol-2H-3-one-1,1-dioxide, which on debenzylation by catalytic hydrogenation gives the corresponding 4-lower-alkoxy-7-hydroxysaccharin of Formula III. Alkylation of a thus prepared 4-lower-alkoxy-7-hydroxy-2-benzyl-1,2-benzoisothiazol-2H-3-one-1-oxide with a lower-alkyl halide or an appropriately substituted lower-alkyl halide followed by oxidation and debenzylation similar affords the corresponding 4-lower-alkoxy-7-$R^3$-saccharin of Formula III wherein $R^3$ is lower-alkoxy, cycloalkoxy, B=N-lower-alkoxy, hydroxy-lower-alkoxy, polyhydroxy-lower-alkoxy or acetal or ketal thereof, lower-alkoxy-poly-lower-alkylenoxy.

In preparing a compound of Formula I wherein L—$R^1$ is substituted or unsubstituted 1,2,3-thiazol-1-yl from the corresponding 2-azidomethyl-4-$R^2$- 5, 6 or 7-$R^3$-sacharrin is cyclized with the corresponding substituted or unsubstituted acetylene in the same solvent at a temperature of 0°–150° C. to give the compound of Formula I.

The pharmaceutically acceptable acid addition salt can be any pharmaceutically acceptable acid addition salt but preferably has a common anion, for example the hydrochloride salt. If the sat having a common anion is unacceptable because it is not crystalline or insufficiently soluble or hygroscopic, a salt having a less common anion, for example the methanesulfonate, can be used. In any event for use in a mammal the acid addition salt must be nontoxic and must not interfere with the elastase inhibitory effect of the free base form of the compound of Formula I.

The pharmaceutically acceptable base addition salt can be any pharmaceutically acceptable base addition salt but preferably has a common cation, for example the sodium or potassium salt. If the salt having a common cation is unacceptable because it i snot crystalline or insufficiently soluble or hygroscopic, a salt having a less common cation, for example the diethylammonium salt, can be used. In any event for use in a mammal the base addition salt must be nontoxic and must not interfere with the elastase inhibitory effect of the free acid form of the compound of Formula I.

The $pK_a$ values of the compounds of formula H—L—$R^1$ are known or can be determined by any of several known methods, for example as described by Adrien Albert and E. P. Serjeant (The Determination of Ionization Constants, A Laboratory Manual, Third Edition, Chapman and Hall, London and New York, 1984) by titration in water (chapters 2 and 3) or by ultraviolet spectrophotometric determination in water (chapter 4), or can be estimated from known or thus determined $pK_a$ values of closely related compounds. CRC Handbook of Chemistry and Physics (72nd Edition, CRC Press, Inc., Boca Raton—Ann Arbor—Boston, 1991, pp. 8-39 and 8-40) presents dissociation constants and pK ($pK_a$) values of several hundred organic acids. G. Kortüm, W. Vogel and K. Andrussow (DISSOCIATION CONSTANTS OF ORGANIC ACIDS IN AQUEOUS SOLUTIONS, Butterworths, London, 1961) presents dissociation constants of 1,056 organic acids.

In the preparations and examples described below structures of products are inferred from known structures of starting materials and expected courses of preparative reactions. Purification or purity and structural confirmation of starting materials and products were carried out or measured by melting temperature range, optical rotation, elemental analysis, infrared spectral analysis, ultraviolet spectral analysis, mass spectral analysis, nuclear magnetic resonance spectral analysis, gas chromatography, column chromatography, high pressure liquid chromatography, medium pressure liquid chromatography and/or thin layer chromatography.

Preparation of
2-Chloromethyl-4-isopropyl-6-methoxysaccharin

To a solution of 300 mL of N,N,N',N'-tetramethylethylenediamine (1.99 moles) in 4 L of anhydrous ether was added 1550 mL of sec-BuLi (1.3 M) and the mixture was cooled to −70° C. under a nitrogen atmosphere. A solution of 454.2 g of 2-isopropyl- 4-methoxy-N,N-diethylbenzamide (1.82 moles) in 300 mL of anhydous ether was added dropwise over 30 minutes. The temperature was maintained at or below −60° C. during the addition. After the addition the mixture was stirred at −70° C. for one hour, allowed to warm to −50° C. held at −50° C. for 30 minutes, then cooled back to −70° C. By cannulation tube a solution of 200 g of $SO_2$ in 200 mL of dry ether precooled to −40° C. was added under positive nitrogen pressure over a 2-minute period. The temperature of the reaction mixture during the addition was maintained below −40° C. A white powdery precipitate of aryllithium sulphinate separated out almost immediately. After the addition the cooling bath was removed and the mixture was stirred at ambient temperature for two hours, then cooled to −5° C. With continued stirring 190 Ml of sulfuryl chloride (2.36 moles) was added dropwise over a 15-minute period while maintaining the temperature below 10° C. After further stirring for 30 minutes at 0°–5° C., a white insoluble precipitate was filtered off and washed with 2 L of anhydrous ether. Removal of the solvent at atmospheric pressure affording the resulting sulfonyl chloride (a crude dark oil) was dissolved in 1.4 L of THF. The solution was cooled to −10° C., and 540 mL of concentrated aqueous ammonia (28%) was added in portions over 15 minutes. The temperature was kept at 15° C. or below throughout the addition. After stirring for 15 minutes at ambient temperature the THF and excess ammonia were removed under vacuum to give a dark oil, which was diluted with 6.0 L of water and acidified with 3N HCl to pH 1. The resulting light yellow solid was collected by filtration, washed with 800 mL of water, dried at 60° C. under vacuum for 18 hours and recrystallized from a mixture of 800 mL of ethyl acetate and 3 L of hexane to give 429 g (72%) of 2-aminosulfonyl-6-isopropyl-4-methoxy-N,N-diethylenzamide, m.r. 122°–125° C.

A solution of 429.6 g of the diethylbenzamide (1.31 mole) in 1.5 L of acetic acid was refluxed for 20 hours, then cooled to room temperature. The solvent was removed under vacuum. The oily residue was dissolved in 6 L of water and the pH was adjusted to 1 with 6N HCl. The crude product was collected by filtration, washed with 2 L of water, dried at 60° C. under vacuum or 18 hours and recrystallized from ethyl acetate/hexane to give 303 g (91%) 4-isopropyl-6-methoxysaccharin, m.p. 188° C.

To a suspension of 24 g of paraformaldehyde (0.8 mole) and 86.4 g of chlorotrimethylsilane (1.6 moles) in 200 mL of 1,2-dichloroethane was added 0.8 ml anhydrous tin(IV) chloride and the resulting solution stirred on a steam bath for one hour. 4-Isorpropyl-6-methoxysaccharin (51.6 g, 0.2 mole) was added to the clear solution and the mixture was refluxed for 18 hours, cooled to room temperature and poured into water. The organic layer was separated, washed with 50 Ml of 2N sodium hydroxide solution, dried over anhydrous magnesium sulfate and concentrated under vacuum. The residue was purified by crystallization from ethyl acetate/hexane to give 57 g (87%) of 2-chloromethyl-4-isopropyl-6-methoxysaccharin, m.p. 151° C.

EXAMPLE 1

2-[4,5-Di(t-butylsulfonyl)-1,2,3-triazol-1-yl]methyl-4-isopropyl-6-methoxysaccharin A solution of 18-crown-6 ether (0.60 g) and benzene (60 mL) was heated under reflux with a water separator for 1 hour, then cooled to room temperature. 2-Chloromethyl-4-isopropyl-6-methoxysaccharin (3.03 g) and sodium azide (0.65 g) were added, and the mixture was stirred for a week at room temperature, then chromatographed on a column of silica gel (silica gel 60, 83 g) using benzene as eluant. The fractions containing the product, which were identified by thin layer chromatography, were combined and concentrated affording 2-azidomethyl-4-isopropyl-6-methoxysaccharin as a solution in benzene (250 mL).

Di(t-butylsulfonyl)acetylene (1.50 g.) was added to part (75 mL) of the above-described solution of 2-azidomethyl-4-isopropyl-6-methoxysaccharin in benzene. The resulting solution was heated under reflux for 65 hours, then chromatographed on silica gel (Kieselgel 60, 68 g) using first benzene and then cyclohexane-ethyl acetate (90:10, then 85:15, then 75:25) as eluant. The fractions containing the product, which were identified by thin layer chromatography, were combined and recrystallized from benzene-cyclohexane. Part (0.5 g) of the resulting product (1.5 g, m.r. 204°–205° C., 26% yield for both steps) was recrystallized twice from ethyl acetate affording 2-[4,5-di(t-butylsulfonyl)- 1,2,3-triazol-1-yl]methyl-4-isopropyl-6-methoxysaccharin as pale yellow elongated prisms (0.15 g, m.r. 207.5°–209° C.).

By tritation in water the $pK_a$ values of 1,2,3-triazole-4,5-dinitrile and 1,2,3-triazole-4,5-dicarboxylic acid dimethyl ester were determined to be 1.6 and 4.4 respectively. By ultraviolet spectrophotometric determination in water the $pK_a$ value of 1,2,3-triazole-4,5-dicarboxyamide was determined to be 5.3. By comparison with these $pK_a$ values the $pK_a$ value of 4,5-di-(t-butylsulfonyl)-1,2,3-triazole is estimated to be about 2 or less.

EXAMPLE 2

2-{2,6-Dichloro-3-[2-(4-morpholinylethoxy)]benzoyloxymethyl}-4-isopropyl-6-methoxysaccharin A mixture of 2-chloromethyl-4-isopropyl-6-methoxysaccharin (3.12 g), 2,6-dichloro-3-[2-(4-morpholinylethoxy)]benzoic acid (3.0 g), potassium carbonate (1.93 g) and tetrabutylammonium bromide (0.75 g) in dimethylformamide (50 mL) was heated at 75° C. for 1.5 hours, cooled to room temperature, and poured into water (400 ml.). The resulting precipitate was collected by filtration, washed with water (200 mL) and hexane (200 mL), and dried affording 2-{2,6-dichloro-3-[2-(4-morpholinylethoxy)]benzoyloxymethyl} -4-isopropyl-6-methoxysaccharin (6.1 g; theory, 5.50 g).

Similar condensation of 2-chloromethyl-4-isopropyl-6-methoxysaccharin and 2,6-dichloro-3-[2-(4-morpholinylethoxy)]benzoic acid with potassium carbonate in N-methylpyrrolidone at room temperature and recrystallization of the product from ethanol afforded 2-{2,6-dichloro-3-[2-(4-morpholinylethoxy)]benzoyloxy-methyl}-4-isopropyl-6-methoxysaccharin in 69% yield (m.p. 146° C.).

Saturated ethereal hydrogen chloride was added to a solution of 2-{2,6-dichloro-3-[2-(4-morpholinylethoxy)]benzoyloxy-methyl}-4-isopropyl- 6-methoxy-saccharin (4.6 g from the first above-described preparation thereof) in etherdichlormethane (9:1, 100 mL). The resulting precipitate was collected by filtration, washed with ether and cyclohexane, and dried affording 2-{2,6-dichloro-3-[2-(4-morpholinylethoxy)] benzoyloxy-methyl}-4-isopropyl-6-methoxysaccharin hydrochloride salt (3.9 g, 89% yield for both steps).

By comparison with known $pK_a$ value of known substituted benzoic acids the $pK_a$ value of 2,6-dichloro-3-[2-(4-morpholinylethoxy)]benzoic acid is estimated to be from about 2 to about 3.

EXAMPLE 3

2-(1-Phenyltetrazol-5-yl)thiomethyl-4-isopropyl-6-methoxysaccharin

A mixture of 2-chloromethyl-4-isopropyl-6-methoxysaccharin (0.25 g) and 1-phenyltetrazole-5-thiol sodium salt (0.173 g) in dimethylformamide (10 mL) was heated at 60°–80° C. for 8 hours, then poured into ice-water containing saturated aqueous sodium bicarbonate. The resulting mixture was extracted with ether. The ether extract was washed with water and saturated aqueous sodium chloride, passed through silica gel and is stripped of ether affording 2-(1-phenyltetrazol-5-yl)thiomethyl-4-isopropyl-6-methoxysaccharin as a foam (0.3 g, 83% yield).

By ultraviolet spectrosphotometric determination in water the $pK_a$ value of 1-phenyltetrazole-5-thiol was determined to be 2.9.

EXAMPLE 4

2-(1-Phenyltetrazol-5-yl)sulfinylmethyl-4-isopropyl-6-methoxysaccharin

Oxidation of 2-(1-phenyltetrazol-5-yl)thiomethyl-4-isopropyl-6-methoxysaccharin with one molar equivalent for m-perbenzoic acid in an inert solvent gives 2-(1-phenyltetrazol-5-yl)sulfinylmethyl-4-isopropyl-6-methoxysaccharin

EXAMPLE 5

2-(1-Phenyltetrazol-5-yl)sulfonylmethyl-4-isopropyl-6-methoxysaccharin

Oxidation of 2-(1-phenyltetrazol-5-yl)sulfinylmethyl-4-isopropyl-6-methoxysaccharin with one molar equivalent of m-perbenzoic acid in an inert solvent gives 2-(1-phenyltetrazol-5-yl)sulfonylmethyl-4-isopropyl-6-methoxysaccharin with one molar equivalent of m-perbenzoic acid in an inert solvent gives 2-(1-phenyltetrazol-5-yl)sulfonylmethyl-4-isopropyl-6-methoxysaccharin.

EXAMPLE 6

2-(4-Phenyl-5-thiono-4,5-dihydrotetrazolyl-1-yl) methyl-4-isopropyl-6-methoxysaccharin Condensation of 4-isopropyl-6-methoxysaccharin sodium salt with 2-chloromethyl-4-phenyl-5-thiono-4,5-dihydrotetrazole in dimethylformamide with heating gives 2-(4-phenyl-5-thiono-4,5-dihydrotetrazolyl-1-yl)methyl-4-isopropyl-6-methoxysaccharin.

EXAMPLE 7

2-Acetoxymethyl-4-isopropyl-6-methoxysaccharin

Condensation of 4-isopropyl-6-methoxysaccharin with aqueous formaldehyde in ethan gives 2 hydroxymethyl-4-isopropyl-6-methoxysaccharin, acetylation of which with acetic anhydride and a catalytic amount of sulfuric acid gives 2-acetoxymethyl-4-isopropyl-6-methoxysaccharin.

Additonal examples of the compounds of Formula I have been prepared by the methods described above and in above-cited applications Ser. No. 07/514,920 and Ser. No. 07/782,016 incorporated herein by reference and are described below in terms of the variable $R_2$, $R_3$ adn $L\!-\!R_1$.

Compounds of Formula I have been prepared wherein $R^2$ is methyl, ethyl, n-propyl, isopropyl, 2-butyl, dimethylamino, methoxy, ethoxy, and isopropoxy.

Compounds of Formula I have been preapred wherein $R^3$ is hydrogen, 7-methyl, 6-(4-methyl-1-piperazinyl), 6-(1-methyl-2-pyrrolyl), 6-dimethylamino, 5-nitro, 6-nitro, 6-hydroxy, 7-hydroxy, 5-methoxy, 6-methoxy, 7-methoxy, 5,6-dimethoxy, 5,7-dimethoxy, 6,7-dimethoxy, 6-ethoxy, 6-isopropoxy, 6-cyclobutyloxy, 6-[2-(4-morpholinyl)ethoxyl], 6-[(2,3-dihydroxy)propoxy], 6-[( 2,3-propylenedioxy)propoxy], 6-[2,3-dimethoxypropoxy], 6-[2-(2-methoxyethoxy)ethoxy], 7[2-(2-methoxyethoxy)ethoxy], 7-carboxymethoxy, 6-methoxycarbonylmethoxy, 6-(t-butoxycarbonyl)methoxy, 6-benzyloxycarbonylmethoxy, 7-(t-butoxycarbonyl)methoxy, 7-dimethylamino-carbonyloxy, 6,7-methylenedioxy, 6-fluoro, 7-chloro, 6-(n-propyl)-7-methoxy, 6-methyl-5,7-dimethoxy, 5-hydroxy-6-methoxy and 6-dimethylamino-7-chloro.

Compounds of Formula I wherein L is N and N taken together with $R^1$ is N-heterocyclyl have been prepared wherein N-heterocyclyl is 4,5-di(t-butylsulfonyl)- 1,2,3-triazol-1-yl, 4-phenyl-5-thiono-4,5-dihydrotetrazolyl-1-yl, 4-(3-pyridyl)-5-thiono- 4,5-dihydrotetrazolyl-1-yl, 1,1,3-trioxotetrahydro-1,2,5-thiadiazol-2-yl, 4,5-di(methoxycarbonyl)-1,2,3-triazol-1-yl, 4-phenylsulfonyl-1,2,3-triazol-1-yl, 4-methoxycarbonyl- 1,2,3-triazol-1-yl, 5-methoxycarbonyl-1,2,3-triazol-1-yl, 4-phenyl-5-ethoxycarbonyl- 1,2,3-triazol-1-yl, 4 ethoxycarbonyl-5-phenyl-1,2,3-triazol-1-yl, 4-carboxy- 1,2,3-triazol-1-yl, 4-trimethylsilyl-5-phenylsulfonyl-1,2,3-triazol-1-yl, 5-phenylsulfonyl-1,2,3-triazol-1-yl, 4-phenylsulfonyl-5-isopropyl-1,2,3-triazin-1-yl, 4-isopropyl-5-phenylsulfonyl-1,2,3-triazol-1-yl, 4,5-di(aminocarbonyl)-1,2,3-triazol-1-yl, 4,5-dicarboxy-1,2,3-triazol-1-yl, 4,5-dicarboxy-1,2,3-triazol-1-yl (monosodium salt), 4-trimethylsilyl-5-dimethylaminosulfonyl-1,2,3-triazol-1-yl, 2-thiono-2,3-dihydro-5-( 2-pyridyl)- 1,3,4-thiadiazol-3-yl, 4-(t-butyl)-5-dimethylaminosulfonyl-1,2,3-triazol-1-yl, 4-dimethylamoniosulfonyl-5-(t-butyl)-1,2,3-triazol-1-yl, 4-trimethylsilyl-1,2,3-triazol-1-yl, 4,5-dicyano-1,2,3-triazol-1-yl, 4,5-di(1-piperidinylcarbonyl)-1,2,3-triazol-1-yl, 4,5-di(trifluoromethyl)-1,2,3-triazol-1-yl, 4,5-di(1-piperidinylcarbonyl)-1,2,3-triazol-2-yl, 3-benzyloxy-4,5-dihydro-5-oxo-1,2,4-oxadiazol-4-yl and 4,5-dicyano-1,2,3-triazol-2-yl.

A compound of Formula I wherein L is O and $R^1$ is lower-alkanoyl has been prepared wherein lower-alkanoyl is 2,2-dimethylpropanoyl.

A compound of Formula I wherein L is O and $R^1$ is an amino acid or peptide acyl has been prepared wherein peptide acyl is (N-benzoylglycyl)phenylalanyl.

A compound of Formula I wherein L is O and $R^1$ is cycloalkanecarbonyl has been prepared wherein cycloalkanecarbonyl is cyclopropanecarbonyl.

Compounds of Formula I wherein L is O and $R^1$ is aryl-lower-alkanoyl unsubstituted or substituted by hydroxy or lower alkoxy have been prepared wherein substituted or unsubstituted aryl-lower-alkanoyl is 2-methyl-2-phenylpropanoyl, 2-methyl- 2-(4-chlorophenyl)propanoyl, 2-(2-chlorophenyl)propanoyl, 2-hydroxy-2-phenylacetyl, 2-methoxy-2-phenylacetyl or 2-hydroxy-2-phenylpropanoyl.

Compounds of Formula I wherein L is O and $R^1$ is monocyclic, substituted or unsubstituted, aromatic or hydroaromatic C-heterocyclylcarbonyl have been prepared wherein C-heterocyclylcarbonyl is 3,5-dichloropyridyl-4-carbonyl, 3,5-dichloro-2-[2-( 4-morpholinyl)ethoxy] pyridyl-4-carbonyl, 3,5-dichloro-2-[2-(dimethylamino)ethoxy] pyridyl-4-carbonyl, thiophene-3-carbonyl, 3-methylthiophene-2-carbonyl, thiophene-2-carbonyl, 3-chlorothiophene-2-carbonyl, 2-oxopyrrolidinyl-5-carbonyl, 3,5-dimethylisoxazol-4-carbonyl, 2,4-dimethylpyridyl-3-carbonyl and 1-phenyl-3,5-dimethylpyrazole- 4-carbonyl.

A compound of Formula I where L is O and $R^1$ is monocyclic substituted aryloxy-2-lower-alkanoyl has been prepared wherein aryloxy-2-lower-alkanoyl is 2-methyl-2-(4-chlorophenoxy)propionyl.

A compound of Formula I wherein L is O and $R^1$ is bicyclic or tricyclic unsubstituted aroyl has been prepared wherein aroyl is 2-naphthoyl or 4-anthracenoyl.

Compounds of Formula I wherein L is O and $R^1$ is monocyclic substituted or unsubstituted aroyl have been prepared wherein monocyclic, substituted or unsubstituted aroyl is 2,6-dichloro-3-[2-(4-morpholinyl)ethoxy]benzoyl, benzoyl, 2,6-dichlorobenzoyl, 2,6-dichloro-3-(4-morpholinylsulfonyl)benzoyl, 2,6-dichloro-3-(4-methyl- 1-piperazinylsulfonyl)benzoyl, 2,6-dichloro-3-(carboxymethylaminosulfonyl)benzoyl, 2,6-dichloro-3-[ N-(4-isopropyl-2-saccharinylmethyl)-N-(benzyloxycarbonyl)amino-sulfonyl] benzoyl, 2,6-dichloro-3-(1-piperazinylsulfonyl)benzoyl, 2,6-dichloro-3-[N-( 2-dimethylaminoethyl-N-(methyl)aminosulfonyl]benzoyl, 2,6-dichloro-3-hydroxybenzoyl, 2,6-dichloro-3-benzyloxybenzoyl, 3-benzyloxybenzoyl, 2,6-dichloro-3-(4-benzyl-1-piperazinylsulfonyl)benzoyl, 2,6-dichloro-3-carboxymethoxybenzoyl, 2,6-dichloro-3-methoxybenzoyl, 2,6-dichloro-4-methoxybenzoyl, 2,6-dichloro-3-[2-

(dimethylamino)ethoxy] benzoyl, 2,6-dichloro-3-[N-(3-dimethylaminopropyl)-N-(methyl)aminosulfonyl] benzoyl, 2,6-di-fluoro-3-(4-methyl-1-piperazinylsulfonyl)benzoyl, 2,4,6-trichlorobenzoyl, 2,6-difluorobenzoyl, 2,6-dimethylbenzoyl, 2,4-dichlorobenzoyl, 2,6-dichloro-4-[2-(4-morpholinyl)ethoxy]benzoyl, 2,6-dichloro-3-[2-( 1-pyrrolidinyl)ethoxy]benzoyl, 2,6-dichloro-3-[2-(1-piperidinyl)ethoxy]benzoyl, 2,6-dichloro-3-[2-(diethylamino)-ethoxy]benzoyl, 2,6-difluoro-4-methoxybenzoyl, 2,6-dimethoxy-4-benzyloxybenzoyl, 2,4,6-trimethoxybenzoyl, 2,6-dichoro-4-ethoxycarbonylbenzoyl, 2-isopropylbenzoyl, 2,6-dimethoxy-4-acetylaminobenzoyl, 2,6-dimethyl-4-benzyloxybenzoyl, 2,6-dimethyl-4-nitrobenzoyl, 2-isopropyl-4-methoxybenzoyl, 2,6-dimethoxy-3-methylsulfonylaminobenzoyl and 2-isopropyl-4,5-dimethoxybenzoyl.

A compound of Formula I wherein L is O and $R^1$ is aryl-lower-alkylaminocarbonyl has been prepared wherein aryl-lower-alkylaminocarbonyl is phenylmethylaminocarbonyl.

A compound of Formula I wherein L is O and $R^1$ is (mono or di-lower-alkyl, phenyl or lower-alkoxyphenyl)phosphinyl has been prepared wherein (mono or di-lower-alkyl, phenyl or lower-alkoxyphenyl)phosphinyl is diphenylphosphinyl.

A compound of Formula I wherein L is O and $R^1$ is (mono or di-lower-alkyl, phenyl or phenyl-lower-alkyl)phosphone has been prepared wherein (mono or di-lower-alkyl, phenyl or phenyl-lower-alkyl)phosphono is diethylphosphono.

Compounds of Formula I wherein L is O and $R^1$ is C-heterocyclyl have been prepared wherein C-heterocyclyl is 2-methyl-4-pyron-3-yl, 6-hydroxymethyl-4-pyron- 3-yl, 3,4-dichloropyridazin-2-yl, 3-phenylcoumarin-7-yl, 4-phenylcoumarin-7-yl, 6-chloro-4-trifluoromethylcoumarin-7-yl, 4-methylcoumarin-7-yl, 3-(benzothiazol-2-yl)coumarin-7-yl, saccharin-6-yl, 4-(4-morpholinyl)-1,2,5-thiadiazol-3-yl, 5-phenyl-1,3,4-thiadiazol- 2-yl, 5-phenyl-1,3,4-oxadiazol-2-yl, 3-methylthio-6-methyl-1,2,4-triazin-5-yl, 4-ethoxycarbonylisoxazol-5-yl, 1,2,5-thiadiazol-3-yl, 2,5-dioxopyrrolidin-1-yl, 2-methyl- 4,5-di(hydroxymethyl)-3-pyridyl, 5-methoxycarbonylisoxazol-3-yl and 1-methyl-2-ethoxycarbonylindol- 3-yl.

Compounds of Formula I wherein L is O and $R^1$ is the residue of oxime were prepared wherein the oxime residue is 2,5-dioxopyrrolidin-1-yl and 3,4-dihydro-3-oxo- 5-phenylpyrazol-4-imino.

A compound of Formula I wherein L is O and $R^1$ is tricyclic substituted aryl was prepared wherein tricyclic substituted aryl is 1-oxo-7-phenalenyl.

Compounds of Formula I wherein L is O and $R^1$ is monocyclic substituted aryl were prepared wherein monocyclic substituted aryl is 2,5-difluoro-4-(4-morpholinylsulfonyl)phenyl, 2,4-dichloro-3-[2-(4-morpholinyl)ethoxycarbonyl)]-phenyl, 2,4-dichlorophenyl, 2,4,6-trichlorophenyl, 2,4-dichloro-3-(4-methylpiperazinylcarbonyl)phenyl, 2,4-dichloro-3-carboxyphenyl, 3-[2-(4-morpholinyl)ethoxycarbonyl)] phenyl, 3-(4-methylpiperazinylcarbonyl)phenyl, 2,4-chloro-3-[2-(4-morpholinyl)ethylaminocarbonyl] phenyl, 4-(4-morpholinylsulfonyl)phenyl, 2,4-dichloro- 6-(4-morpholinylsulfonyl)phenyl, 2-chloro-4-(4-morpholinylsulfonyl)phenyl, 2-methoxycarbonyl-5-methoxyphenyl, 2-fluoro-4-(4-morpholinylsulfonyl)phenyl, 2-chloro-4-(4-thiamorpholinylsulfonyl)phenyl, 2-chloro-4-(4,4-dioxy-4-thiamorpholinylsulfonyl)phenyl, 2,6-difluoro-4-(4-morpholinylsulfonyl)phenyl, 2,4-difluoro-6-(4-morpholinylsulfonyl)phenyl, 3,4-difluoro-6(4-morpholinylsulfonyl)phenyl, 2-(4-morpholinylsulfonyl)-4-fluorophenyl, 4-[2-(4-morpholinyl)ethylaminocarbonyl] phenyl, pentafluorophenyl, 3-(4-methylpiperazinylsulfonyl)phenyl, 3-(4-morpholinylethoxy)phenyl, 3-[2-(dimethylamino)ethyl)methyl-aminosulfonyl]phenyl, 4-methylsulfonylphenyl, 3-diethoxyphosphonylphenyl, 2-trifluoromethyl-4-(4-morpholinylsulfonyl)phenyl, 2,6-dichloro-4-(4,5-dihydro-oxazol-2yl)phenyl, 3,5-difluoro-4-(4-morpholinylcarbonyl)phenyl, 3,5-difluorophenyl, 2,5-difluoro-4-(4-methylpiperazinylsulfonyl)phenyl, 2,6-dichloro-4-ethoxycarbonylphenyl, 1-oxocycloheptatrien-2-yl and 3,5,6-trimethylquinone-2-yl.

A compound of Formula I wherein L is O and $R^1$ is monocyclic, substituted, hydroaromatic 3-oxycarbonyl-1-enyl has been prepared wherein 3-oxycarbonyl-1-enyl is 2-methyl-3-oxo-1-cyclopentyl.

A compound of Formula I wherein L is O and $R^1$ is monocyclic, substituted, aromatic 3-oxo-C-heterocycl-1-enyl has been prepared wherein 3-oxo-C-heterocycl- 1-enyl is 6-methyl-1-pyron-4-yl.

Compounds of Formula I wherein L is S and $R^1$ is cyano, benzoyl and ethoxythiocarbonyl have been prepared.

Compounds of Formula I wherein L is S, SO or $SO_2$ and $R^1$ is monocyclic substituted aryl has been prepared wherein monocyclic substituted aryl is 2-fluoro-4-(4-morpholinylsulfonyl)phenyl.

Compounds of Formula I where L is S and $R^1$ is monocyclic, substituted, aromatic C-heterocyclyl have been prepared wherein monocyclic, substituted, aromatic C-heterocyclyl is 1-phenyltetrazol-5-yl, 1-[2-(4-morpholinyl)ethyl] tetrazol-5-yl, 1-(dimethylaminocarbonyl-methyl)tetrazol-5-yl, 1-(3-pyridyl)tetrazol-5-yl, 1-methyltetrazol-5-yl, 5-methyl-1,3,4-thiadiazol-2-yl, 5-cyclohexylamino-1,3,4-thiadiazol- 2-yl, 1-(4-morpholinylpropyl)-tetrazol-5-yl, 5-[2-(4-morpholinyl)ethylthio]- 1,3,4-thiadiazol-yl, 5-(2-dimethylaminoethylthio)-1,3,4-thiadiazol-yl, 5-[2-(4-morpholinyl)ethyl] -1,3,4-thiadiazol-2-yl, 5-[2-(1-piperidinyl)ethyl]-1,3,4-thiadiazol-2-yl, 5-phenyl-1,3,4-oxadiazol-2-yl, 5-(2-furyl)-1,3,4-oxadiazol-2-yl, 1-( 3-succinoylaminopheny)-tetrazol- 5-yl, 5-benzyl-1,3,4-oxadiazol-2-yl, 5-hydroxy-6-methyl-6,7-dihydro- 1H-1,2,4-triazolo[3,4-b] [1,3]thiazin-3-yl, 5-(3-pyridyl)-1,3,4-oxadiazol-2-yl, 1-methyl-5-ethoxy- 1,3,4-triazol-2-yl, 5-(4-trifluoromethylphenyl)-1,3,4-oxadiazol-2-yl, 5-(4-methoxyphenyl)-1,3,4-oxadiazol-2-yl, 5-(4-pyridyl)-1,3,4-oxidiazol-2-yl, 5-(4-diphenylyl)-1,3,4-oxadiazol-2-yl, 5-(2-pyrazinyl)-1,3,4-oxadiazol-2-yl, 4-(ethoxycarbonylmethyl)thiazol-2-yl, 5-(2-pyridyl)-1,3,4-oxadiazol-2-yl, 5-(3-furyl)- 1,3,4-oxadiazol-2-yl, 4-ethoxycarbonyl-5-methylthiazol-2-yl, 4-phenylthiazol-2-yl, 4,5-dimethylthiazol-2-yl, 4-(4-morpholinyl)-1,2,5-thiadiazol-2-yl, 3-phenyl-2-thiono- 2,3-dihydro- 1,3,4-thiadiazol-5-yl, 4-methyl-5-oxo-6-hydroxy-4, 5-dihydro-1,2,4-triazin-3-yl, 5-[4-(n-pentyloxy)phenyl]-1,3, 4-oxadiazol-2-yl, 5-{4-[2-(2-methoxyethoxy)ethoxy] phenyl}-1,3,4-oxadiazol-2-yl, 5-(3,4-methylenedioxyphenyl)-1,3,4-oxadiazol-2-yl, 5-(2,5-dimethoxyphenyl)-1,3,4-oxadiazol-2-yl, 5-(2-methoxyphenyl)-1,3,4-oxadiazol-2-yl and 5-phenyloxazol-2-yl.

Biological Properties of the Compounds

As stated above the compounds of Formula I inhibit the enzymatic activity of proteolytic enzymes and are useful in treatment of degenerative diseases. More particularly they inhibit human leukocyte elastase and chymotrypsin-like enzynmes and are useful in treatment of emphysema, rheumatoid arthritis, pancreatitis, cystic fibrosis, chronic bronchitis, adult respiratory distress syndrome, inflammatory bowel disease, psoriasis, bullous pemphigoid and alpha-1-antitrypsin deficiency. This utility was demonstrated by an in vitro test of inhibition of compounds of Formula I against human leukocyte elastase.

Measurement of the inhibition constant ($K_i$) of a human leukocyte elastase inhibitor complex has been described (Cha, Biochemical Pharmacology, vol 24, pp. 2177– 2185, 1975) for "truly reversible inhibition constants" usually concerning competitive inhibitors. The compounds of Formula I do not form truly reversible inhibitor complexes but rather are consumed by the enzyme to some extent. $K_i I$, which is defined as the rate of reactivation of the enzyme divided by the rate of inactivation of the enzyme ($k_{off}/k_{on}$), was therefore determined instead. The values of $k_{off}$ and $k_{on}$ were measured and $K_i^*$ was then calculated.

The value of $k_{on}$ was determined by measuring the enzyme activity of an aliquot of the enzyme as a function of the time after addition of the test compound (inhibitor). By plotting the log of the enzyme activity against time an observed rate of inactivation ($k_{obs}$) was obtained by the equation $k_{obs} = \ln 2/t_{1/2}$ wherein $t_{1/2}$ is the time required for the enzyme activity to decrease by 50%. The value of $k_{on}$ was then obtained by the equation $k_{on} = k_{obs}/[I]$ wherein [I] is the concentration of the inhibitor. The value of $k_{off}$ was similarly determined, and $K_i^*$ was then obtained by the equation $K_i^* = k_{off}/k_{on}$.

The results shown in Table I were obtained for the compounds of Formula I of Examples 1–3.

TABLE I

| Inhibition of Human Leukocyte Elastase | |
| --- | --- |
| Compound of Formula I of Example | $K_i^*$ (nM) |
| 1 | 0.024 |
| 2 | 0.014 |
| 3 | 0.27 |

The other examples of the compounds of Formula I have $K_i^*$ value in the range from about 1,00 nM to about 0.01 nM.

Method of Use and Compositions

The proteolytic enzyme inhibiting amount of the compound of Formula I can be estimated from the results of the test for human leukocyte elastase inhibition and can additionally be varied for a particular patient depending on the physical condition of the patient, the route of administration, the duration of treatment and the response of the patient. An effective dose of the compound of Formula I can thus only be determined by the clinician after consideration of all pertinent criteria and exercise of best judgment on behalf of the patient.

A compound of Formula I can be prepared for pharmaceutical use by incorporating it in a pharmaceutical composition of oral, parenteral or aerosol inhalation administration, which can be in solid or liquid dosage form including tablets, capsules, solutions, suspensions and emulsions and which can include one or more suitable adjuvants. Solid unit dosages in the form of tablets or capsules for oral administration are preferred. For this purpose the adjuvant can be for example one or more of calcium carbonate, starch, lactose, talc, magnesium stearate and gum acacia. The compositions are prepared by conventional pharmaceutical techniques.

We claim:

1. A compound having the structural formula

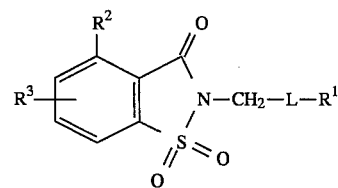

wherein

L—$R^1$ is a substituted or unsubstituted triazolyl;

$R^2$ is primary or secondary alkyl of two to four carbon atoms, primary alkylamino of one to three carbon atoms, primary alkylmethylamino of two to four carbon atoms, diethylamino or primary alkoxy of one to three carbon atoms; and $R^3$ is from one to three substituents at any or all of the 5-, 6- and 7-positions and is selected from the group consisting of hydrogen, lower-alkyl, cycloalkyl, amino lower-alkyl, lower-alkylamino-lower-alkyl, di-lower-alkylamino-lower-alkyl, hydroxy-lower-alkyl, lower-alkoxy-lower-alkyl, perfluoro-lower-alkyl, perchloro-lower-alkyl, formyl, cyano, carboxy, aminocarbonyl, R-oxycarbonyl, B═N wherein B═N is amino, lower-alkylamino, di-lower alkylamino, carboxy-lower-alkylamino, 1-pyrrolidinyl, 1-piperdinyl, 1-azetidinyl, 4-morpholinyl, 1-piperazinyl, 4-lower-alkyl-1-piperazinyl, 4-benzyl-1-piperazinyl or 1-imidazolyl, 1-lower-alkyl-2-pyrrolyl, lower alkylsulfonylamino, perfluoro-lower-alkylsulfonylamino, perchloro-lower alkylsulfonylamino, nitro, hydroxy, lower-alkoxy, cycloalkoxy, B═N-lower-alkoxy, hydroxy-lower-alkoxy, polyhydroxy-lower-alkoxy, or acetal or ketal thereof, lower-alkoxy-lower-alkoxy, poly-lower-alkoxy lower-alkoxy, hydroxy-poly-lower alkylenoxy, lower-alkoxy-poly-lower-alkylenoxy, B═N-carbonyloxy, carboxy-lower-alkoxy, R-oxycarbonyl lower-alkoxy, methylenedioxy, di-lower-alkylphosphonyloxy, R-thio, R-sulfinyl, R-sulfonyl, perfluoro-lower-alkylsulfonyl, perchloro-lower alkylsulfonyl, aminosulfonyl, lower-alkylaminosulfonyl, di-lower alkylaminosulfonyl and halo wherein R is lower-alkyl, phenyl, benzyl or naphthyl or phenyl or naphthyl having one or two substituents selected from the group consisting of lower-alkyl, lower-alkoxy and halo;

or a pharmaceutically acceptable acid addition salt thereof if the compound has a basic functional group or a pharmaceutically acceptable base addition salt thereof if the compound has an acidic functional group.

2. A compound according to claim 1 wherein $R^2$ is primary or secondary alkyl of two to four carbon atoms.

3. A compound according to claim 1 wherein $R^2$ is isopropyl.

4. A compound according to claim 3 wherein $R^3$ is hydroxy, lower-alkoxy, cycloalkoxy, B═N-lower-alkoxy, hydroxy-lower-alkoxy, polyhydroxy-lower-alkoxy or acetal or ketal thereof, lower-alkoxy-lower-alkoxy, poly-lower-alkoxy-lower-alkoxy, lower-alkoxy-poly-lower-alkoxy, B═N-carbonyloxy, carboxy-lower-alkoxy, R-oxycarbonyl-lower-alkoxy, or methylenedioxy.

5. A compound according to claim 4 wherein $R^3$ is lower-alkyl.

6. A compound according to claim 5 wherein $R^3$ is methoxy.

7. A compound according to claim 6 wherein $R^3$ is 6-methoxy.

8. A compound according to claim 7 wherein L is N and H—L—$R^1$ has a $pK_a$ value less than or equal to 6.

9. A compound of claim 1 wherein the triazolyl is substituted with one or two of the following: butylsulfonyl; methoxycarbonyl; phenylsulfonyl; phenyl, ethoxycarbonyl; carboxy; trimethylsilyl; isopropyl; aminocarbonyl; dicarboxy; dimethylaminosulfonyl; t-butyl; cyano; 1-piperdinylcarbonyl; or trifluoromethyl.

10. A compound of claim 1 wherein L—R¹ is 1,2,3-triazo-1-yl or 1,2,3-triazo-2-yl having substituted thereon, 4,5-di(t-butylsulfonyl); 4,5, di(methoxycarbonyl); 4-phenylsulfonyl; 4-methoxycarbonyl; 5-methoxycarbonyl; 4-phenyl-5-ethoxycarbonyl; 4-ethoxycarbonyl- 5-phenyl; 4-carboxy; 4-trimethylsilyl-5-phenylsulfonyl; 5-phenylsulfonyl; 4-isopropyl-5-phenylsulfonyl; 4,5-di(aminocarbonyl); 4,5-dicarboxy; 4-trimethylsilyl- 5-dimethylaminosulfonyl; 4-(t-butyl)-5-dimethylaminosulfonyl; 4-dimethylaminosulfonyl-5-(t-butyl); 4-trimethylsilyl; 4,5-dicyano; 4,5-di(1-piperdinylcarbonyl); or 4,5-di(trifluoromethyl).

11. A compound of claim 1 wherein L—R1 is 4,5-di(t-butylsulfonyl)- 1,2,3-triazo-1-yl; 4,5,di(methoxycarbonyl)-1,2,3-triazo- 1-yl; 4-phenylsulfonyl-1,2,3-triazo-1-yl; 4-methoxycarbonyl-1,2,3-triazo- 1-yl; 5-methoxycarbonyl-1,2,3-triazo-1-yl; 4-phenyl-5-ethoxycarbonyl- 1,2,3-triazo-1-yl; 4-ethoxycarbonyl-5-phenyl-1,2,3-triazo- 1-yl; 4-carboxy-1,2,3-triazo-1-yl; 4-trimethylsilyl-5-phenylsulfonyl-1,2,3-triazo-1-yl; 5-phenylsulfonyl-1,2,3-triazo-1-yl; 4-isopropyl-5-phenylsulfonyl- 1,2,3-triazo-1-yl; 4,5-di(aminocarbonyl)-1,2,3-triazo- 1-yl; 4,5dicarboxy-1,2,3-triazo-1-yl; 4-trimethylsilyl-5-dimethylaminosulfonyl- 1,2,3-triazo-1-yl; 4-(t-butyl)-5-dimethylaminosulfonyl- 1,2,3-triazo-1-yl; 4-dimethylaminosulfonyl-5-(t-butyl)- 1,2,3-triazo-1-yl; 4-trimethylsilyl-1,2,3-triazo-1-yl; 4,5-dicyano-1,2,3-triazo-1-yl; 4,5-di(1-piperdinylcarbonyl)-1,2,3-triazo- 1-yl; 4,5-di(trifluoromethyl)-1,2,3-triazo-1-yl; 4,5-di(1-piperdinylcarbonyl)- 1,2,3-triazo-2-yl; or 4,5-dicyano-1,2,3-triazo-2-yl.

12. A compound of claim 1 wherein the triazolyl is 1,2,3-triazo-1-yl.

13. The compound of 2-[4,5-di(t-butylsulfonyl)-1,2,3-triazol-1-yl] methyl-4-isopropyl-6-methoxysaccharin or a pharmaceutically acceptable salt thereof.

14. A pharmaceutical composition for the treatment of generative disease which comprises a proteolytic inhibiting concentration of a compound in a pharmaceutical carrier, wherein the compound has the structure:

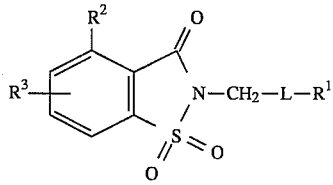

wherein

L—R¹ is a substituted or unsubstituted triazolyl;

R² is primary or secondary alkyl of two to four carbon atoms, primary alkylamino of one to three carbon atoms, primary alkylmethylamino of two to four carbon atoms, diethylamino or primary alkoxy of one to three carbon atoms; and R³ is from one to three substituents at any or all of the 5-, 6- and 7-positions and is selected from the group consisting of hydrogen, lower-alkyl, cycloalkyl, amino lower-alkyl, lower-alkylamino-lower-alkyl, di-lower-alkylamino-lower-alkyl, hydroxy-lower-alkyl, lower-alkoxy-lower-alkyl, perfluoro-lower-alkyl, perchloro-lower-alkyl, formyl, cyano, carboxy, aminocarbonyl, R-oxycarbonyl, B═N wherein B═N is amino, lower-alkylamino, di-lower alkylamino, carboxy-lower-alkylamino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl, 1-lower-alkyl-2-pyrrolyl, lower alkylsulfonylamino, perfluoro-lower-alkylsulfonylamino, perchloro-lower alkylsulfonylamino, nitro, hydroxy, lower-alkoxy, cycloalkoxy, B═N-lower-alkoxy, hydroxy-lower-alkoxy, polyhydroxy-lower-alkoxy, or acetal or ketal thereof, lower-alkoxy-lower-alkoxy, poly-lower-alkoxy lower-alkoxy, hydroxy-poly-lower alkylenoxy, lower-alkoxy-poly-lower-alkylenoxy, B═N-carbonyloxy, carboxy-lower-alkoxy, R-oxycarbonyl lower-alkoxy, methylenedioxy, di-lower-alkylphosphonyloxy, R-thio, R-sulfinyl, R-sulfonyl, perfluoro-lower-alkylsulfonyl, perchloro-lower alkylsulfonyl, aminosulfonyl, lower-alkylaminosulfonyl, di-lower alkylaminosulfonyl and halo wherein R is lower-alkyl, phenyl, benzyl or naphthyl or phenyl or naphthyl having one or two substituents selected from the group consisting of lower-alkyl, lower-alkoxy and halo;

or a pharmaceutically acceptable acid addition salt thereof if the compound has a basic functional group or a pharmaceutically acceptable base addition salt thereof if the compound has an acidic functional group.

15. A compound of claim 14 wherein the triazolyl is substituted with one or two of the following: butylsulfonyl; methoxycarbonyl; phenylsulfonyl phenyl; ethoxycarbonyl; carboxy; trimethylsilyl; isopropyl; aminocarbonyl; dicarboxy; dimethylaminosulfonyl; t-butyl; cyano; 1-piperdinylcarbonyl; or trifluoromethyl.

16. A compound of claim 14 wherein L—R¹ is 1,2,3-triazo-1-yl or 1,2,3-triazo-2-yl having substituted thereon, 4,5-di(t-butylsulfonyl); 4,5, di(methoxycarbonyl); 4-phenylsulfonyl; 4-methoxycarbonyl; 5-methoxycarbonyl; 4-phenyl-5-ethoxycarbonyl; 4-ethoxycarbonyl- 5-phenyl; 4-carboxy; 4-trimethylsilyl-5-phenylsulfonyl; 5-phenylsulfonyl; 4-phenylsulfonyl-5-isopropyl; 4-isopropyl- 5-phenylsulfonyl; 4,5-di(aminocarbonyl); 4,5-dicarboxy; 4-trimethylsilyl-5-dimethylaminosulfonyl; 4-(t-butyl)-5-dimethylaminosulfonyl; 4-(t-butyl)-5-dimethylaminosulfonyl; 4-dimethylaminosulfonyl-5-(t-butyl); 4-trimethylsilyl; 4,5-dicyano; 4,5-di(1-piperdinylcarbonyl); or 4,5-di(trifluoromethyl).

17. A compound of claim 14 wherein L—R1 is 4,5-di(t-butylsulfonyl)- 1,2,3-triazo-1-yl; 4,5, di(methoxycarbonyl)-1,2,3-triazo- 1-yl; 4-phenylsulfonyl-1,2,3-triazo-1-yl; 4-methoxycarbonyl-1,2,3-triazo- 1-yl; 5-methoxycarbonyl-1,2,3-triazo-1-yl; 4-phenyl-5-ethoxycarbonyl- 1,2,3-triazo-1-yl; 4-ethoxycarbonyl-5-phenyl-1,2,3-triazo- 1-yl; 4-carboxy-1,2,3-triazo-1-yl; 4-trimethylsilyl-5-phenylsulfonyl-1,2,3-triazo-1-yl; 5-phenylsulfonyl-1,2,3-triazo-1-yl; 4-phenylsulfonyl-5-isopropyl-1,2,3-triazo-1-yl; 4-isopropyl-5-phenylsulfonyl- 1,2,3-triazo-1-yl; 4,5-di(aminocarbonyl)-1,2,3-triazo- 1-yl; 4,5-dicarboxy-1,2,3-triazo-1-yl; 4-trimethylsilyl-5-dimethylaminosulfonyl- 1,2,3-triazo-1-yl; 4-(t-butyl)-5-dimethylaminosulfonyl- 1,2,3-triazo-1-yl; 4-dimethylaminosulfonyl-5-(t-butyl)- 1,2,3-triazo-1-yl; 4-trimethylsilyl-1,2,3-triazo-1-yl; 4,5-dicyano-1,2,3-triazo-1-yl; 4,5-di(1-piperdinylcarbonyl)-1,2,3-triazo- 1-yl; 4,5-di(trifluoromethyl)-1,2,3-triazo-1-yl; 4,5-di(1-piperdinylcarbonyl)- 1,2,3-triazo-2-yl; or 4,5-dicyano-1,2,3-triazo-2-yl.

18. A compound of claim 14 wherein the triazolyl is 1,2,3-triazo-1-yl.

* * * * *